(12) United States Patent
Mallette

(10) Patent No.: US 8,496,477 B2
(45) Date of Patent: Jul. 30, 2013

(54) DENTAL PROSTHETIC AND RESTORATION REMOVAL SYSTEM AND METHOD

(76) Inventor: Kermit Joseph Mallette, Peachtree City, GA (US)

( * ) Notice: Subject to any disclaimer, the term of this patent is extended or adjusted under 35 U.S.C. 154(b) by 152 days.

(21) Appl. No.: 12/686,370

(22) Filed: Jan. 12, 2010

(65) Prior Publication Data

US 2012/0021378 A1  Jan. 26, 2012

Related U.S. Application Data

(60) Provisional application No. 61/144,014, filed on Jan. 12, 2009.

(51) Int. Cl.
*A61C 3/00* (2006.01)

(52) U.S. Cl.
USPC .......................................... 433/154; 433/141

(58) Field of Classification Search
USPC .................. 433/3, 141, 25, 40–45, 145–147, 433/152–162; 606/99, 130, 205–209
See application file for complete search history.

(56) References Cited

U.S. PATENT DOCUMENTS

| | | | | |
|---|---|---|---|---|
| 2,430,271 A | * | 11/1947 | Brantley | 433/154 |
| 2,682,109 A | * | 6/1954 | Roux, Jr. | 433/154 |
| 3,579,834 A | * | 5/1971 | Reed, Jr. | 433/154 |
| 5,197,877 A | * | 3/1993 | Andrew | 433/153 |
| 5,411,396 A | * | 5/1995 | Frei | 433/153 |

* cited by examiner

*Primary Examiner* — Cris L Rodriguez
*Assistant Examiner* — Matthew Seward
(74) *Attorney, Agent, or Firm* — Leslie A. Thompson; Leslie A. Thompson & Associates

(57) ABSTRACT

A system for removing dental prosthetics and restorations effectively and efficiently without damaging the dental prosthetic or restoration and with minimal discomfort to a patient is disclosed. The system features central holder designed for receiving and securely supporting a single or plurality of support arms in a spaced apart arrangement, whereby each support arm is capable of supporting an adjustable and pivoting attachment designed to adhesively engage and remove a dental prosthetic and restoration with the application of force. The system also features a plurality of independent attachments that can be used to adhesively engage and effectively remove a dental prosthetic and restoration with the application of force.

20 Claims, 13 Drawing Sheets

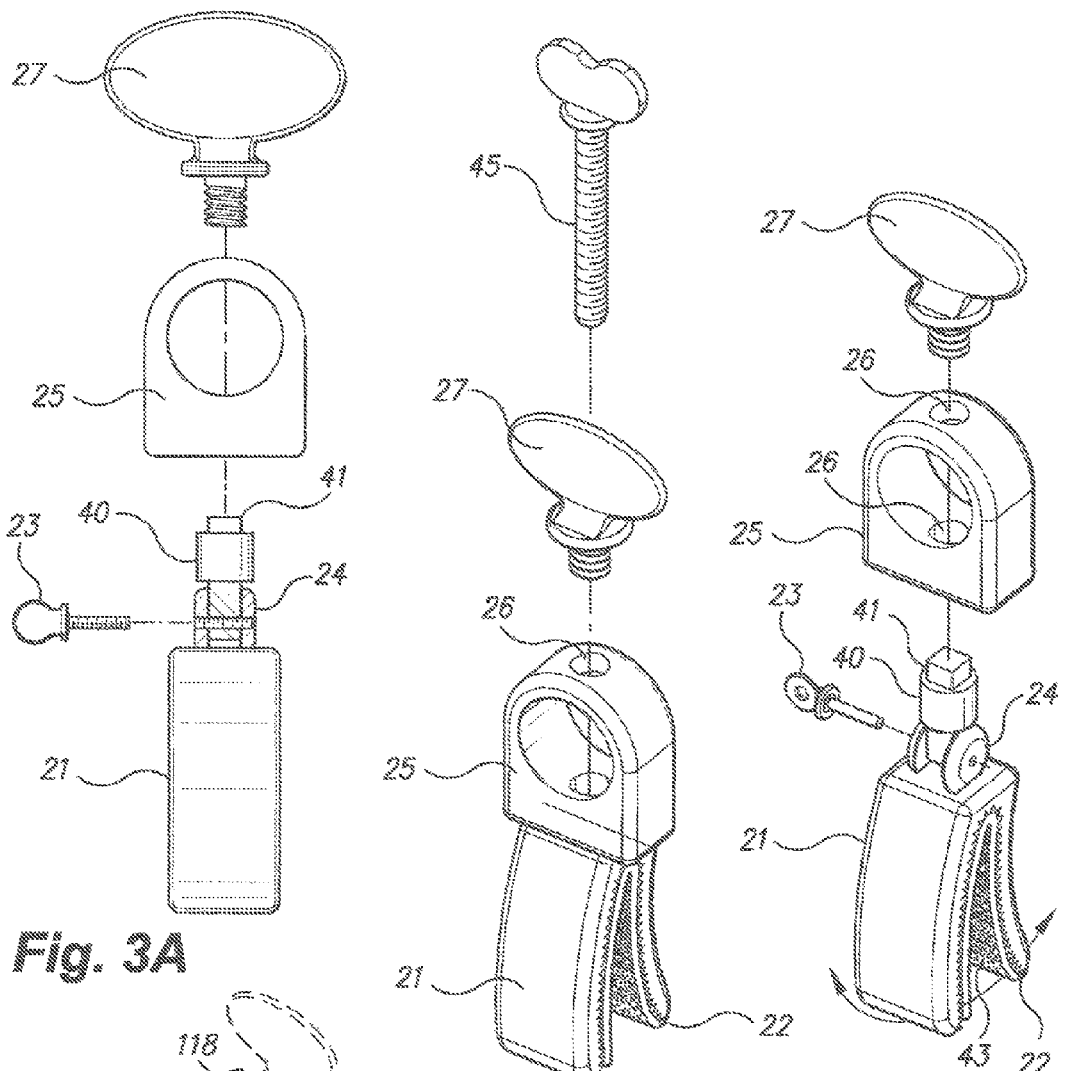
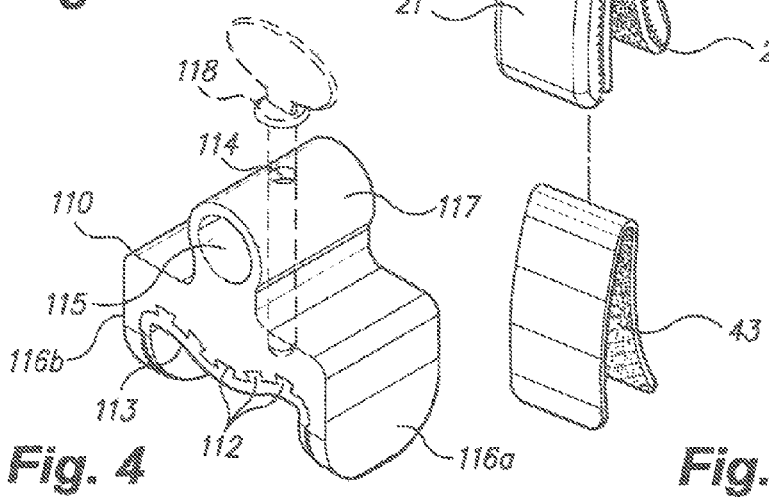
Fig. 3A Fig. 3B Fig. 4 Fig. 5

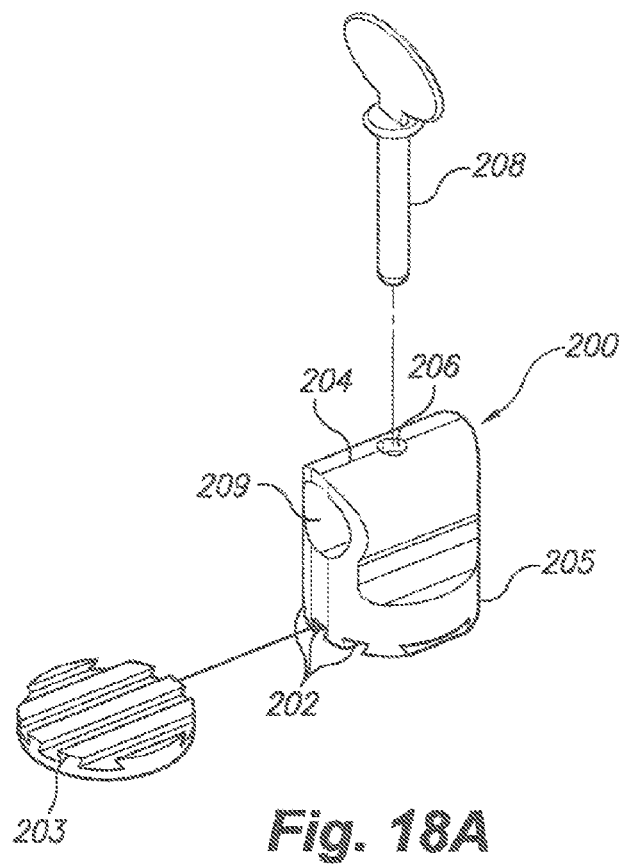
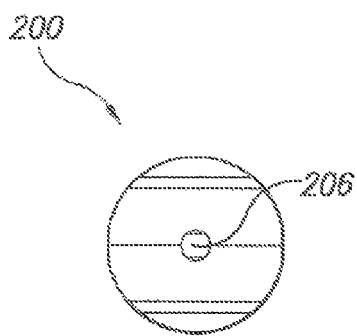
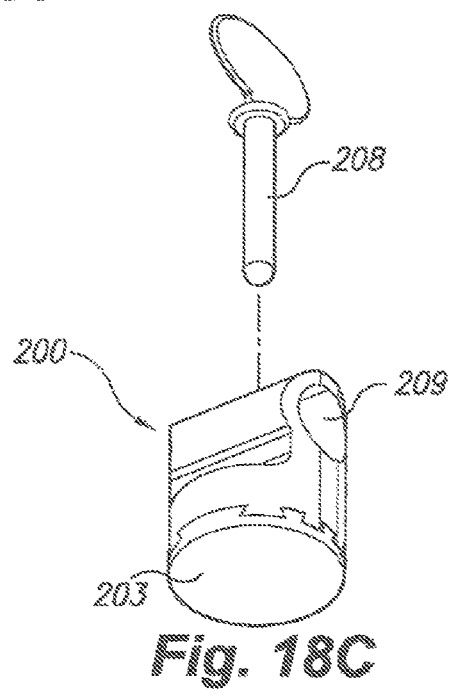

DENTAL PROSTHETIC AND RESTORATION REMOVAL SYSTEM AND METHOD

REFERENCE TO RELATED APPLICATION

This application claims priority to U.S. Provisional Application No. 61/144,014 filed on Jan. 12, 2009, the entire content of which is incorporated herein by reference.

FIELD OF THE INVENTION

The present invention relates to dental prosthetics and restorations and more particularly, to a system for effectively and efficiently removing a plurality of dental prosthetics and restorations without damaging the dental articles and with minimal discomfort to a patient.

BACKGROUND OF INVENTION

Removal of crowns, bridges, inlays, onlays, and other dental prosthetics and restorations is routine dentistry. The preferred methods for removal of dental prosthetics and restorations, such as crowns, are to cut a crown off or to wedge a crown-tapping device under the margin, which might damage the crown. When a crown needs to be removed from an oral cavity in the event the seal for the crown has been compromised or the crown needs to be repaired or adjusted, it is important to prevent damage to the crown during the act of removal. If the crown is damaged during removal, reconstruction or replacement of the crown would result in substantial expense which should be avoided. In light of the fragility of crowns, a dental practitioner must often rely upon the strength of his or her fingers to effect removal since extraction implements which have a low probability of causing damage to the crown do not exist. All dental practitioners do not have sufficient strength in their fingers to effect the removal of a crown. Furthermore, the space or volume available within the oral cavity to manually grip a crown may be a limiting factor of the ease with which a crown can be removed by manual manipulation.

BRIEF DESCRIPTION OF THE DRAWINGS

FIG. 3A is an exploded plan view of the anterior tooth attachment of the dental prosthetic and restoration removal system according to the present invention.

FIG. 3B is an exploded environmental perspective view of the anterior tooth attachment of the dental prosthetic and restoration removal system according to the present invention.

FIG. 4 is an environmental perspective view of a first alternative embodiment of the posterior tooth attachment of the dental and restoration removal system according to the present invention.

FIG. 5 is an exploded environmental perspective view of an alternative embodiment of the anterior tooth attachment according to the dental prosthetic and restoration removal system according to the present invention.

FIG. 18A is an environmental perspective of the quadrant tooth attachment of the dental prosthetic and restoration removal system according to the present invention.

FIG. 18B is a top plan view of the quadrant tooth attachment of the dental prosthetic and restoration removal system according to the present invention.

FIG. 18C is a bottom environmental perspective of the quadrant tooth attachment of the dental prosthetic and restoration removal system according to the present invention.

DETAILED DESCRIPTION

The present invention is a dental prosthetic and restoration removal system 10 and method comprising a plurality of dental attachments that a dentist can employ to effectively and efficiently remove a plurality of dental prosthetics and restorations without damaging the dental prosthetics and restorations and with minimal discomfort to a patient.

Figure 1A:
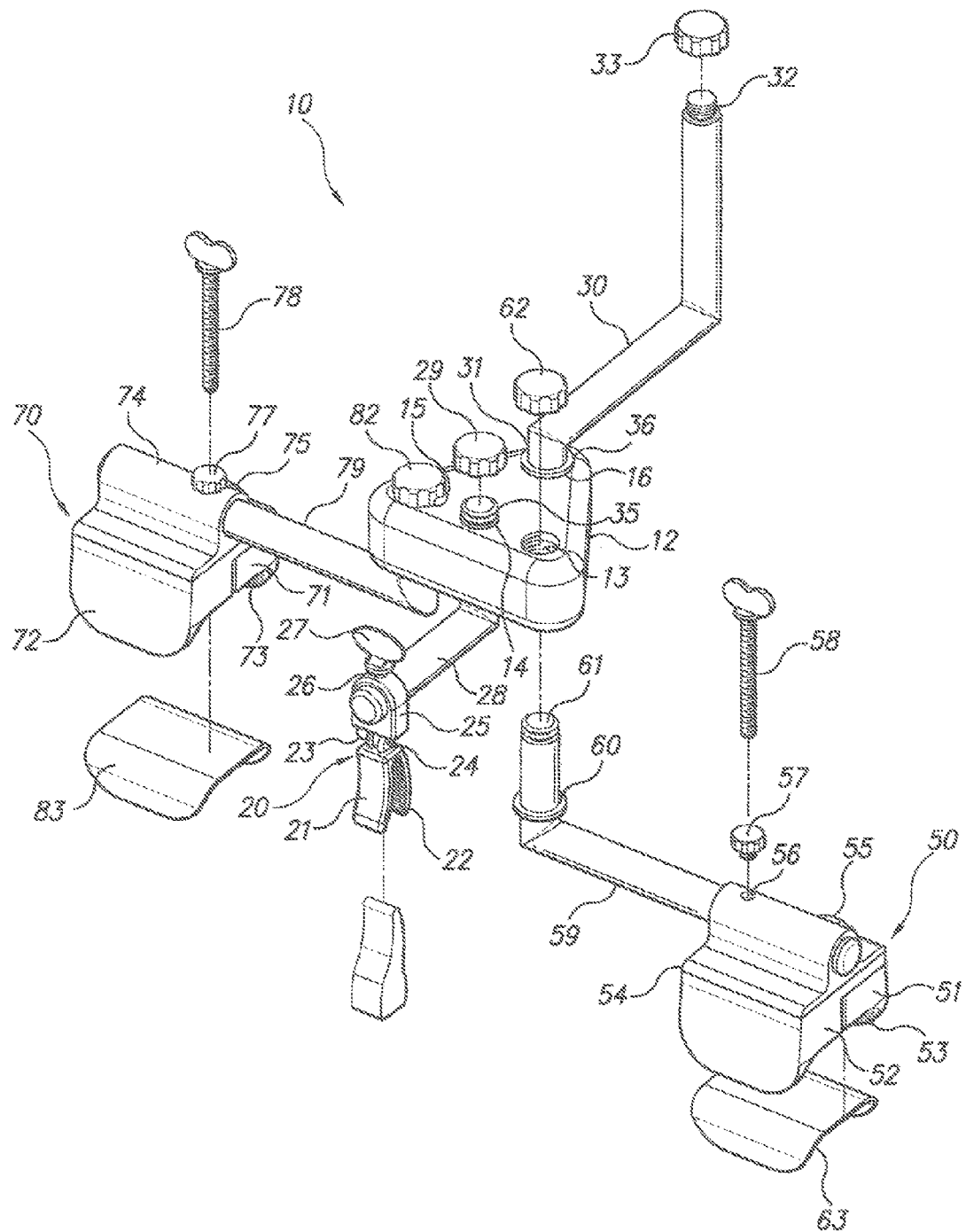
FIG. 1A is a front environmental perspective view of the dental prosthetic and restoration removal system according to the present invention.
Figure 1B:
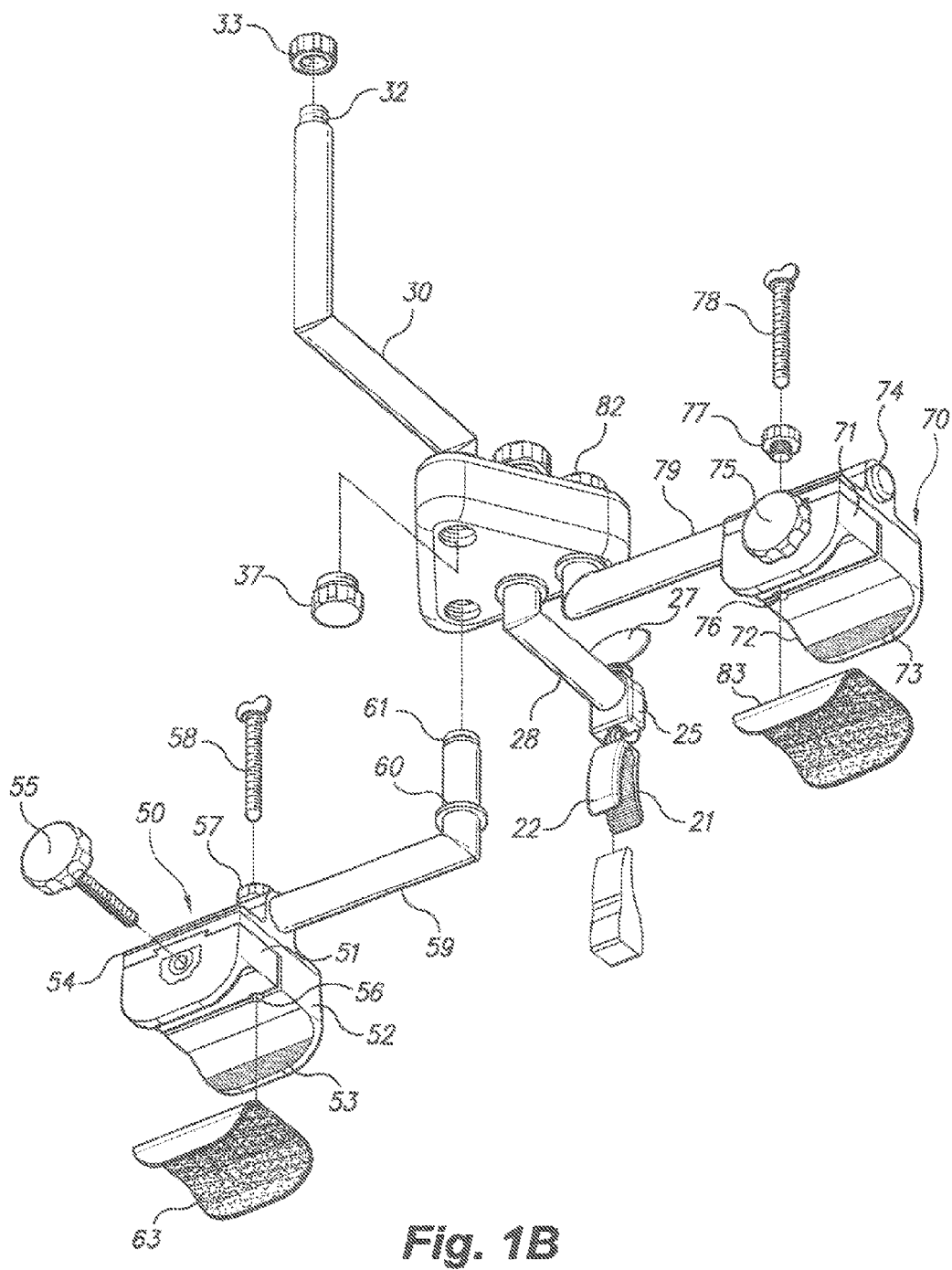
FIG. 1B is a rear environmental perspective view of the dental prosthetic and restoration removal system according to the present invention.

As best seen in FIGS. 1A and 1B, the dental prosthetic and restoration removal system 10 of the present invention comprises a generally triangular central holder 12 from which depends a plurality of elongated L-shaped force bars 59,79 which support a plurality of prosthetic or restoration attachments 50,70, which shall generally be referred to as "tooth (teeth) attachments" throughout this description of the present invention. The preferred embodiment of dental prosthetic and restoration removal system 10 is designed to remove a full arch or round house bridge where a pair of similarly structured adjustable posterior tooth attachments 50,70 is aligned to attach to posterior molar teeth with a single adjustable anterior tooth attachment 20 disposed therebetween for coupling to anterior teeth. Proprietary adhesive substances 63,83, similar to sticky candy, are uniquely shaped for use by dental professionals in conjunction with this system 10 for the removal of dental prosthetics and restorations. Conventional adhesives used in dental prosthetic and restoration removal can be adapted for use with the instant invention.

The central holder 12 is a generally triangular housing having three rounded corners. A plurality of apertures 13,15, 16 are uniformly disposed through the body of central holder 12 in each rounded corner. These apertures 13,15,16 are designed to frictionally receive the cylindrical support arms 59,79,30 of the posterior tooth attachments 50,70 and the force mechanism 30, respectively. In the preferred embodiment, an additional aperture 14 is disposed through the body of central holder 12 and is uniformly between apertures 13,15. Aperture 14 is designed to frictionally receive support arm 28 of the anterior tooth attachment 20.

The support arms 28,59,79 of anterior tooth attachment 20 and posterior tooth attachments 50,70, respectively, are generally L-shaped cylindrical bars having a proximate end and a distal end. The proximate ends of the support arms 28,59,79 are threaded at the tip and are designed to frictionally penetrate the apertures 14,13,15. Each proximate end of support arms 28,59,79 is further defined by an annular lip disposed around the proximate shorter portion of the support arm generally near the perpendicular bend in each support arm. As best seen with posterior tooth attachment 50 in FIGS. 1A-1B, an annular lip 60 is disposed around the proximate end near the perpendicular bend in support arm 59. The annular lip 60 is sufficiently wide enough and arranged to serve as a stop when the proximate end of the support arm 59 is received in aperture 13, such that only threaded tip 61 of support arm 59 is visible beyond the upper surface of central holder 12. A threaded screw cap 62 is threadingly engaged to tip 61 to prevent displacement of the support arm 59. Once the screw cap 82 is secured, the frictional engagement of support arm 50 in aperture 13 allows a dental practitioner to laterally move the support arm 59 with the application of sufficient manual force. Posterior tooth attachment 70 is the structural equivalent of posterior tooth attachment 50. The threaded proximate end (not shown here) of posterior tooth attachment 70 is threadingly engaged by screw cap 82 above the upper surface of central holder 12. The threaded proximate end 35 of anterior tooth attachment 20 is threadingly engaged by screw cap 29 above the upper surface of central holder 12. As seen in FIG. 1B, the annular lip 28a disposed around the proximate end of anterior tooth attachment 20 serves to stop penetration of support arm 28 in aperture 14. In a manner similar to support arm 59 of posterior tooth attachment 50, the support arms 28,79 can be moved laterally with the application of sufficient manual force.

As seen in FIGS. 1A-1B, the force bar 30 is a generally cylindrical construction having a middle bar portion with perpendicular extensions on each end and oriented in opposite directions with respect to one another. The tip 32 of the perpendicular extension on the proximate end of force bar 30 is threaded to threadingly engage screw cap 33 or the matable end of a conventional weighted force mechanism. The tip (not shown here) of the perpendicular extension at the distal end of force bar 30 is internally threaded. An annular lip 36 arranged around the distal perpendicular extension causes the tip to stop flush with the bottom of central holder 12 when the distal perpendicular extension is frictionally received in aperture 16. As best seen in FIG. 1B, a threaded fastener 37 is threadingly mated with the internally threaded tip of the distal perpendicular extension, thereby fixedly securing the force bar 30 with respect to central holder 12.

As seen in FIGS. 1A, 1B, and 3B, prior to the insertion of the device 10 in the oral cavity, proprietary adhesive substances 43,63,83 specifically designed to conform to the contoured underside 22, 53,73 of generally V-shaped portion 21 of the anterior tooth attachment 20 and one or both of the generally block-shaped posterior tooth attachments 50,70, respectively, are thermally treated and forcibly placed on underside 22,53,73 of aforementioned tooth attachments 20,50,70. Application of the proprietary adhesives 63,83,43 allow a dental practitioner to temporarily couple the posterior tooth attachment(s) 50,70 and/or anterior tooth attachment 20 to a full arch or round house bridge or a single posterior or anterior crown or other dental prosthetic or restoration. The underside areas 22,53,73 of both the anterior tooth attachment 20 and posterior tooth attachments 50,70, respectively, can be molded with gripping elements to facilitate the securing of the uniquely shaped proprietary adhesives 43,63,83 thereto.

As mentioned earlier with regards to FIG. 1, an anterior tooth attachment 20 is disposed between the pair of posterior tooth attachments 50,70 and designed to attach to the incisor teeth with the assistance of a uniquely shaped proprietary adhesive substance 43 (See FIG. 2) (similar to sticky candy) placed on the underside 22 of the generally V-shaped tooth-engaging portion 21 of the anterior tooth attachment 20. A uniquely shaped proprietary adhesive substance 43 can be placed directly on the anterior tooth or forcibly applied to the underside 22 of the anterior tooth attachment 20 in order to temporarily couple the anterior tooth attachment 20 to a single crown or tooth.

Both the anterior tooth attachment 20 and posterior tooth attachments 50,70 are designed to fit any prosthetic arch through mechanical manipulation of the device 10. The device 10 can then be attached to a desired force mechanism of the dental practitioner which will deliver sufficient force necessary to remove a temporary or permanently cemented bridge, for example, or other dental prosthetic or restoration. Alternatively, the respective anterior tooth attachment 20 and posterior tooth attachments 50,70 can be used individually and separately from the generally triangular central holder 12 to remove dental prosthetics and restorations.

Figure 2A:
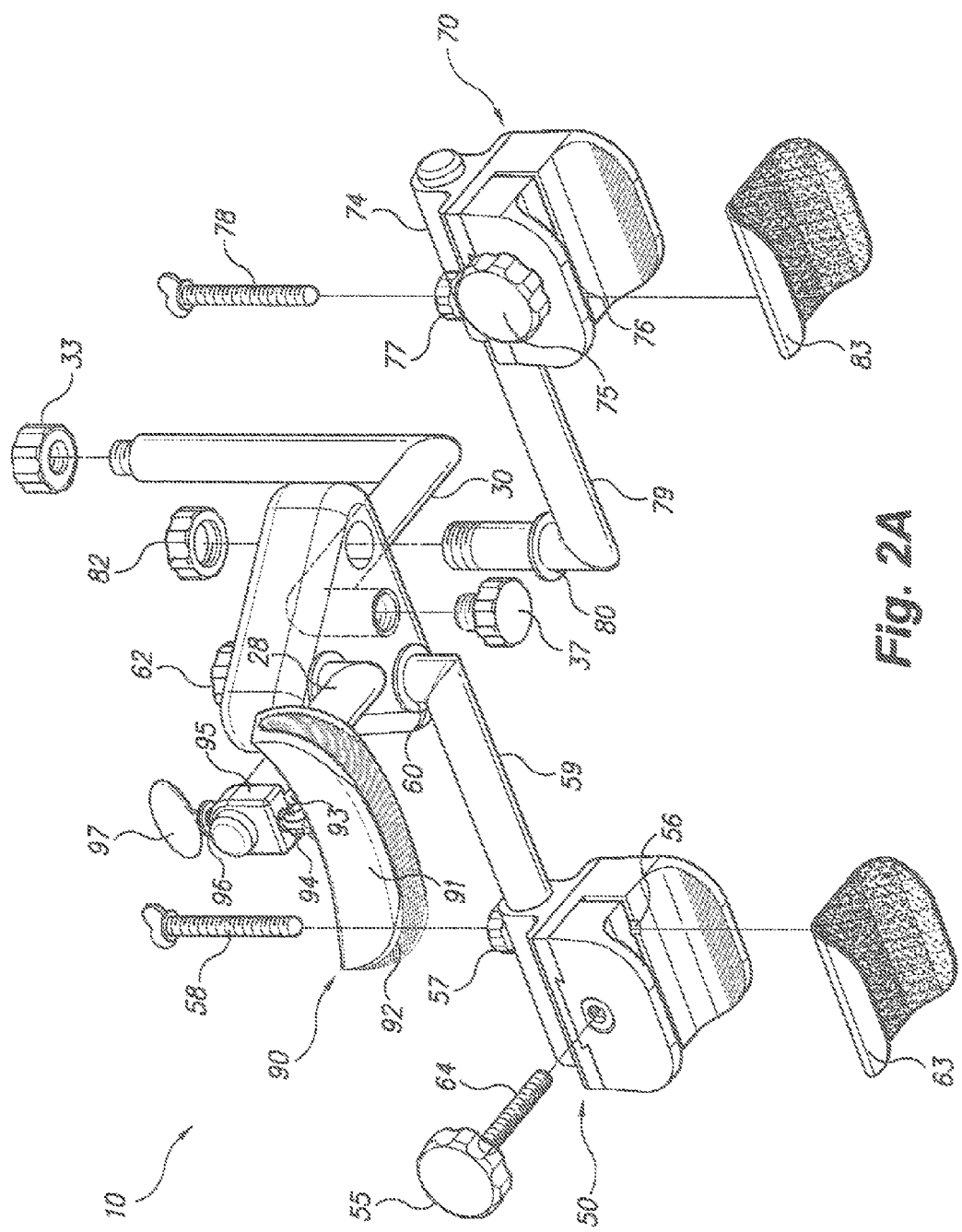
FIG. 2A is a front environmental perspective view of an alternative embodiment of the dental prosthetic and restoration removal system according to the present invention.
Figure 2B:
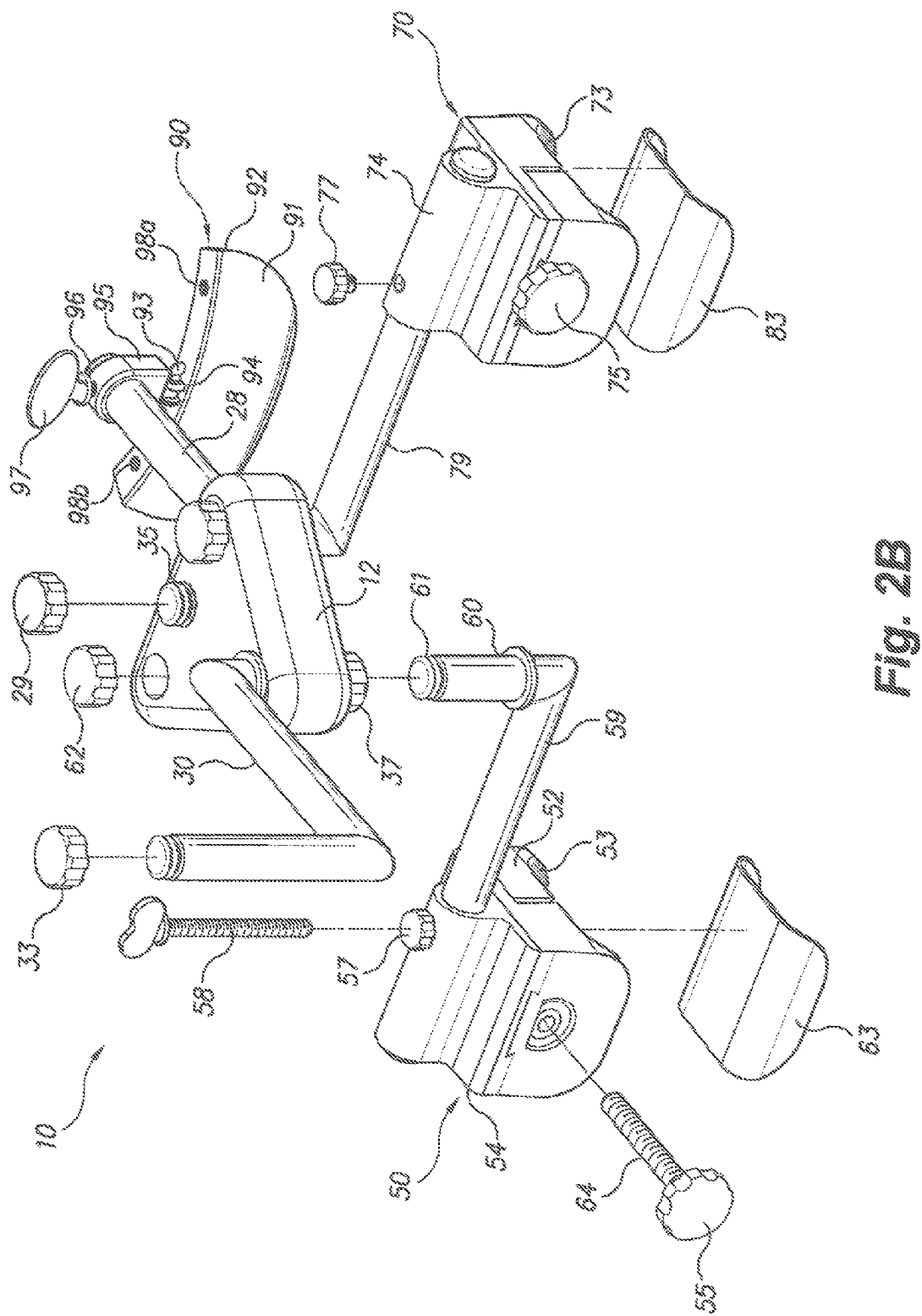
FIG. 2B is a rear environmental perspective view of an alternative embodiment of the dental prosthetic and restoration removal system according to the present invention.

Referring to FIGS. 2A-2B, the dental prosthetic and restoration removal system 10 of the present invention teaches an anterior teeth attachment 90 having a pivoting generally elongated arcuate member 91. Member 91 of anterior teeth attachment 90 is designed to arcuately extend to several of the anterior prosthetic teeth for more distribution of force in the anterior dentition as desired by the dental practitioner.

The dental prosthetic and restoration removal system 10 of the present invention includes an anterior teeth attachment 90 comprising an elongated arcuate member 91 having a generally V-shaped configuration that is designed to engage a dental prosthetic or restoration spanning a plurality of anterior teeth. The arcuate member 91 of anterior teeth attachment 90 is pivotally arranged to a crown member 95 to allow for buccal-lingual adjustment. A pivoting mechanism 94 has a shaft that is fixedly attached at one end to the bottom of the crown member 95 and has a central aperture (not shown here) laterally disposed therein. The center of the top surface of arcuate member 91 is defined by two spaced members designed to frictionally receive the opposing end of the shaft of the pivoting mechanism. The two spaced apart members vertically disposed on the top wall of arcuate member 91 each have a central aperture that corresponds to the central aperture of the shaft of pivoting mechanism 94 when the shaft is frictionally received therebetween. The pivoting mechanism is arranged such that introduction of a cylindrical anchoring pin 93 through the aligned apertures of the shaft and spaced apart members causes the arcuate member 91 to be secured at the desired angle of orientation. Removal of anchoring pin 93 facilitates angularly reorienting arcuate member 91. Reinsertion of anchoring pin 93 thereafter facilitates securing arcuate member 91 in the new angular orientation.

A tightening screw 97 threadingly disposed through a threaded aperture 96 in the rounded top sidewall of crown member 95 is used to secure the anterior teeth attachment 90 to a support arm 28 inserted through a central aperture in the body of crown member 95. Tightening screw 97 is used to prevent buccal-lingual movement of the anterior teeth attachment 90 when properly inserted in the oral cavity.

Arcuate member 91 of anterior teeth attachment 90 has corresponding threaded apertures 98a,98b disposed through the top wall near the opposing ends of arcuate member 91. Each threaded aperture 98a,98b is designed to receive an emergency removal screw (not shown here) which assists the dental practitioner in removing the anterior teeth attachment 90 from the anterior teeth after the dental prosthetic/restoration has been engaged and the anterior teeth attachment 90 cannot be extracted with the preferred method of removal. Tightening screw 97 and support arm 28 must be removed and the emergency removal screws are respectively introduced through threaded apertures 98a,98b in the top sidewall of arcuate member 91. This placement of the emergency screws allows the dental practitioner to manually extract the anterior teeth attachment from the oral cavity with minimal to no damage to the engaged dental prosthetic/restoration or anterior teeth. As the emergency removal screws are manually engaged, the distal ends of the emergency removal screws penetrate the proprietary adhesive substance (not shown here) until the distal ends are supported atop the targeted crown or other dental prosthetic/restoration and the anterior teeth attachment 90 is urged off the targeted dental prosthetic/restoration in a cervico-occlusal direction.

A dental practitioner may selectively interchange the single anterior tooth attachment 20 and the anterior teeth attachment 90 with device 10 as required.

FIGS. 3A-3B show the anterior tooth attachment 20 (as seen also seen in FIGS. 1A-1B) which allows the dental practitioner to remove a single crown (or applicable restoration) from an anterior tooth. Anterior tooth attachment 20 includes a crown 25, a pivoting mechanism, and a generally V-shaped tooth-engaging member 21. The tooth-engaging member 21 of anterior tooth attachment 20 is pivotally arranged to crown member 25 to allow for buccal-lingual adjustment by the dental practitioner. A pivoting mechanism 24 has a shaft 40 that is fixedly attached at one end 41 to the bottom of the crown member 25 and has a central aperture laterally disposed therein. The center of the top wall of tooth-engaging member 21 is defined by two spaced members designed to frictionally receive the opposing end of the shaft 40 of pivoting mechanism 24. The two spaced apart members vertically disposed on the top wall of tooth-engaging member 21 each have a central aperture that corresponds to the central aperture of shaft 40 when shaft 40 is frictionally received therebetween. The pivoting mechanism is arranged such that introduction of a cylindrical anchoring pin 23 through the aligned apertures of shaft 40 and spaced apart members causes the tooth-engaging member 21 to be secured at the desired angle of orientation. Removal of anchoring pin 23 facilitates angularly reorienting arcuate member 91. Reinsertion of anchoring pin 93 thereafter facilitates securing tooth-engaging member 21 in the new angular orientation.

A tightening screw 27 is introduced through a threaded aperture 26 disposed through the top sidewall of crown member 25 of anterior tooth attachment 20 is used to secure the anterior tooth attachment 20 to support arm 28 (not shown here) inserted through a central aperture laterally disposed through body of crown 25. Engagement of tightening screw 27 is used to prevent buccal-lingual movement of the anterior tooth attachment 20 once properly inserted in the oral cavity.

As seen in FIG. 3B, the preferred embodiment of the anterior tooth attachment 20 is pivotally arranged to facilitate buccal-lingual movement (as the directional arrows indicate) of the anterior tooth attachment 20 to accommodate engagement with anterior prosthetic teeth with a buccal or lingual orientation. Once the tooth-engaging member 21 is properly adjusted for placement on buccal or lingual anterior teeth, the anchoring pin 23 is reinserted in the pivoting mechanism 24 to lock the tooth-engaging member 21 in the desired angular orientation.

As seen in FIG. 4, an alternative embodiment of the posterior tooth attachment 110 is used for single tooth molar crown removal. This posterior tooth attachment 110 comprises a base which supports an integral barrel sleeve 117 on the upper surface and includes an underside having downwardly depending sidewalls 116a,116b with a plurality of recessed grooves 112 formed therebetween that extend longitudinally in upper surface of underside for greater retention of a proprietary adhesive substance 113 applied to the underside. A threaded aperture 114 located at the midpoint of posterior tooth attachment 110 extends vertically through top and bottom walls of integral barrel sleeve 117 onward through the base. Posterior tooth attachment 110 is ideally used for posterior crown removal, but is adaptable for the removal of other dental prosthetics and restorations. When a support arm (not shown here) is introduced through the opening 115 of the integral barrel sleeve 117, a tightening screw (not shown here) is introduced through threaded aperture 114 disposed in the top wall of integral barrel sleeve 117 until the tightening screw engages the support arm to releasably secure the position of posterior tooth attachment 110 on the support arm. In the event proprietary adhesive 113 placed on the underside of posterior tooth attachment 110 has bonded posterior tooth attachment 110 to the engaged crown (or applicable restoration)—the dental practitioner may not be able to remove posterior tooth attachment 110 with the preferred method, but still must take proper care not to torque or luxate the underlying tooth or teeth in a manner that will damage or improperly extract said tooth or teeth. Hence, the tightening screw and support arm are removed from posterior tooth attachment 110 by the dental practitioner. An elongated emergency removal screw 118 (as seen in the broken lines) can be introduced through threaded aperture 114 in the top wall of integral barrel sleeve 117 and threadingly mated with a corresponding threaded aperture in the base of posterior tooth attachment 110. As emergency removal screw 118 is manually engaged, the distal end of emergency removal screw 118 penetrates the proprietary adhesive substance 113 until the distal end is supported atop the targeted crown. Subsequently, posterior tooth attachment 110 is urged off the targeted crown in a cervico-occlusal direction. Thus allowing the dental practitioner to manually extract the posterior tooth attachment 110 from the oral cavity with minimal to no damage to the engaged crown or prosthetic teeth.

As seen in FIG. 5, an alternative anterior tooth attachment 100 is configured as a single static assembly where the V-shaped tooth-engaging portion 21 is statically fixed to the bottom of the crown member 25 with no pivotal movement. A proprietary adhesive substance 43 is placed on the underside of the tooth-engaging member 21 of the alternative anterior tooth attachment 100. A tightening screw 27 is introduced through a threaded aperture 26 disposed through the top sidewall of crown member 25 of anterior tooth attachment 100 is used to secure the anterior tooth attachment 100 to support arm 28 (not shown here) inserted through a central aperture laterally disposed through body of crown 25. Engagement of tightening screw 27 is used to prevent buccal-lingual movement of the anterior tooth attachment 100 once properly inserted in the oral cavity.

In the event proprietary adhesive 43 placed on the underside of anterior tooth attachment 100 has bonded anterior tooth attachment 100 to the engaged crown (or applicable restoration)—the dental practitioner may not be able to remove anterior tooth attachment 100 with the preferred method, but still must take proper care not to torque or luxate the underlying tooth or teeth in a manner that will damage or improperly extract said tooth or teeth. Hence, the tightening screw and support arm are removed from anterior tooth attachment 100 by the dental practitioner. An elongated emergency removal screw 45 can be introduced through threaded aperture 26 in the top wall of crown 25 and threadingly mated with a corresponding threaded aperture 26 in the base of crown 25. As emergency removal screw 45 is manually engaged, the distal end of emergency removal screw 45 penetrates the proprietary adhesive substance 43 until the distal end is supported atop the targeted crown. Subsequently, anterior tooth attachment 100 is urged off the targeted crown in a cervico-occlusal direction. Thus allowing the dental practitioner to manually extract anterior tooth attachment 100 from the oral cavity with minimal to no damage to the engaged crown or prosthetic teeth.

Figure 6:
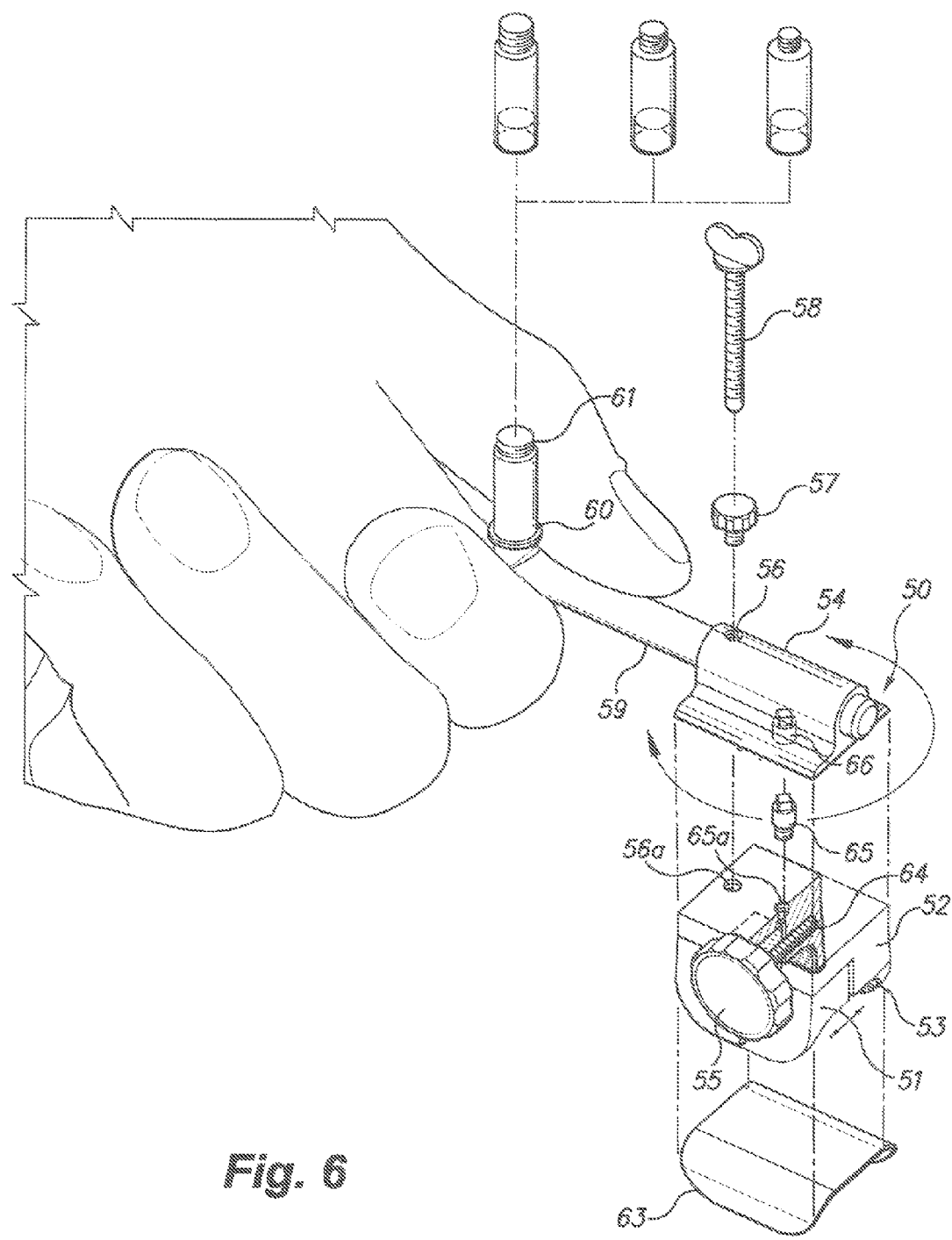
FIG. 6 is an exploded environmental perspective view of a posterior tooth attachment of the dental prosthetic and restoration removal system according to the present invention.

As seen in FIG. 6, the preferred embodiment of the posterior tooth attachment 50,70 is designed with buccal-lingual adjustability which aids the dental practitioner with engaging posterior tooth attachment 50 with various buccal-lingual widths. Posterior tooth attachment 50 is bifurcated such that an upper portion 54 and a lower portion 52 are rotationally coupled with respect to one another. The upper portion 54 compromises a base having an upper surface that supports an integral barrel sleeve with a circular opening. The lower portion 52 comprises a two-section housing where the respective components 51,52 abut in a modular flush arrangement at the midsection and are horizontally positioned and adjusted with respect to one another by a screw mechanism 55. An internal aperture (not shown) completely traverses the first section 51 and partially traverses the second section 52 in a corresponding position in a threaded manner. The threaded shaft 64 of a screw 55 is introduced into the internal aperture through the sidewall of first section 51 and threadingly travels internally to mate with the corresponding threaded aperture in the second section 52. When the generally planar head of the threaded screw 55 is manually engaged and rotated until said screw 55 is flush with the sidewall of first section 52, the two sections 51,52 flushedly abut. When the generally planar head of the screw 55 is manually engaged and rotated in the opposite direction, the two sections 51,52 become spaced apart to accommodate the necessary buccal-lingual adjustments the dental practitioner must make to engage a particular posterior prosthetic tooth or applicable dental prosthetic or restoration.

As previously mentioned and seen in FIG. 6, upper portion 54 and lower portion 52 of posterior tooth attachment 50 are rotationally coupled to accommodate necessary buccal-lingual adjustments the dental practitioner must make to engage a particular posterior tooth or teeth or applicable dental prosthetic or restoration. Generally corresponding at the midpoint 66 of bottom surface of the base of upper portion 54 and the midpoint 65a of the upper surface of second section of lower portion 52, a swivel or rotational means 65 couples upper portion 54 to lower portion 52. The lower portion 52 can be rotated about the swivel means 65 to adjust for buccal-lingual displacement of targeted prosthetic tooth.

Referring to FIG. 6, the upper portion 54 has a threaded aperture 56 at the proximate end that vertically traverses the upper portion 54 and corresponds with a threaded aperture 56 in the lower portion 51,52 at the proximate end. When the support arm 59 is introduced through the proximate end of the opening of the integral barrel sleeve of upper portion 54, a tightening screw 57 is introduced through the threaded aperture 56 disposed in the top of the integral barrel sleeve until tightening screw 57 engages support arm 59 to releasably secure the position of upper portion 54 on support arm 59. In the event the proprietary adhesive substance 63 placed on the contoured underside 53 of posterior tooth attachment 50 has bonded posterior tooth attachment 50 to the engaged prosthetic tooth or teeth, the dental practitioner may not be able to remove said attachment with the preferred method. The dental practitioner must still take proper care not to torque or luxate the tooth or teeth in a manner that will damage or improperly extract said tooth or teeth. Hence, the tightening screw 57 and support arm 59 must be removed and an elongated emergency removal screw 58 is introduced through threaded aperture 56 in the proximate upper portion 54 and mated with the corresponding threaded aperture 56 (as seen in FIG. 1b) in the proximate lower portion 51,52. This allows the dental practitioner to manually extract the device from the oral cavity with minimal to no damage to the engaged teeth or dental prosthetic or restoration(s).

As seen in FIG. 6, the threaded tip 61 of the proximate end of support arm 59 can be mated with a plurality of adapters to accommodate a plurality of conventional force mechanisms.

Figure 7:
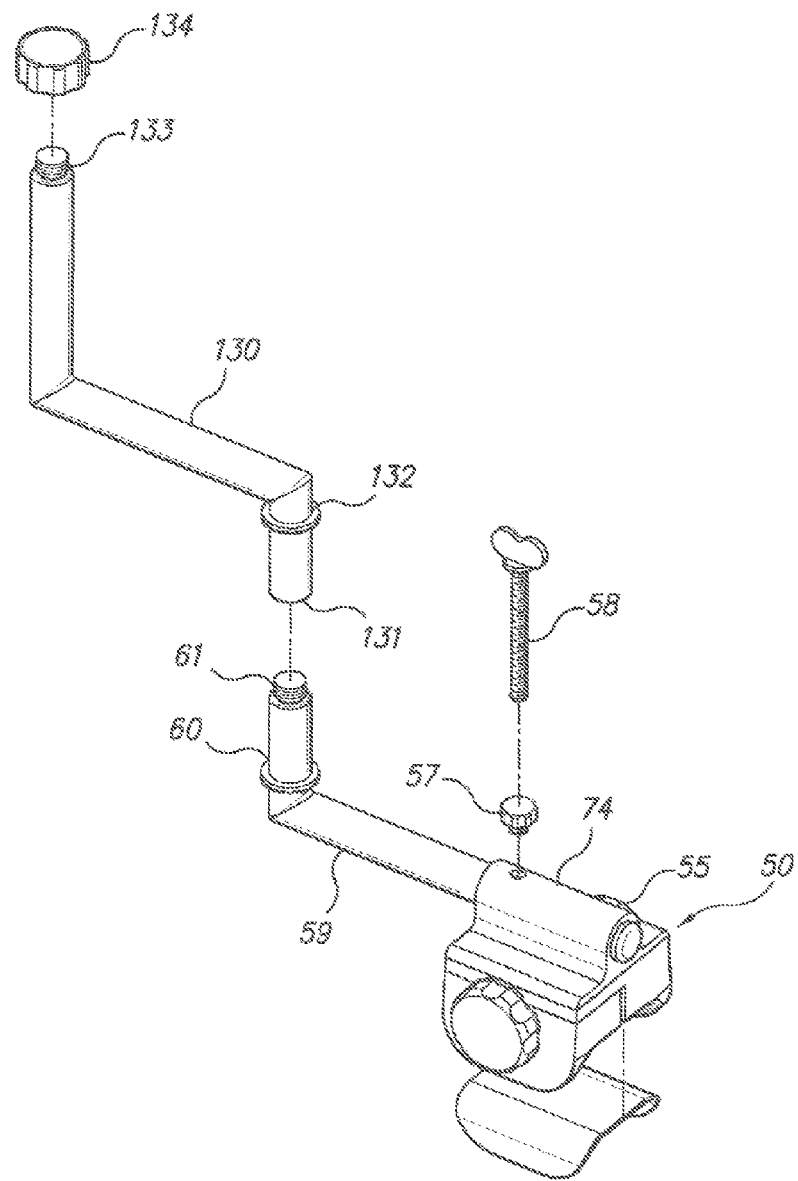
FIG. 7 is an environmental perspective view an alternative application of the posterior tooth attachment of the dental prosthetic and restoration removal system according to the present invention.

Referring to FIG. 7, a force bar extension 130 can be coupled to threaded tip 61 of support arm 59 on posterior tooth attachment 50 in order to extend the force mechanism away from the face of a patient if the patient demonstrates extreme fear or anxiety of the procedure. The force bar extension 130 is a generally cylindrical construction having a middle bar portion with perpendicular extensions on each end and oriented in opposite directions with respect to one another. The tip 133 of the perpendicular extension on the proximate end of force bar extension 130 is threaded to engage a threaded screw cap 134 or the matable end of a conventional weighted force mechanism. The tip (not shown here) of the perpendicular extension at the distal end of force bar extension 130 is internally threaded and can be threadingly engaged to threaded tip 61 of support arm 59 for secure placement thereon.

Figure 8A:
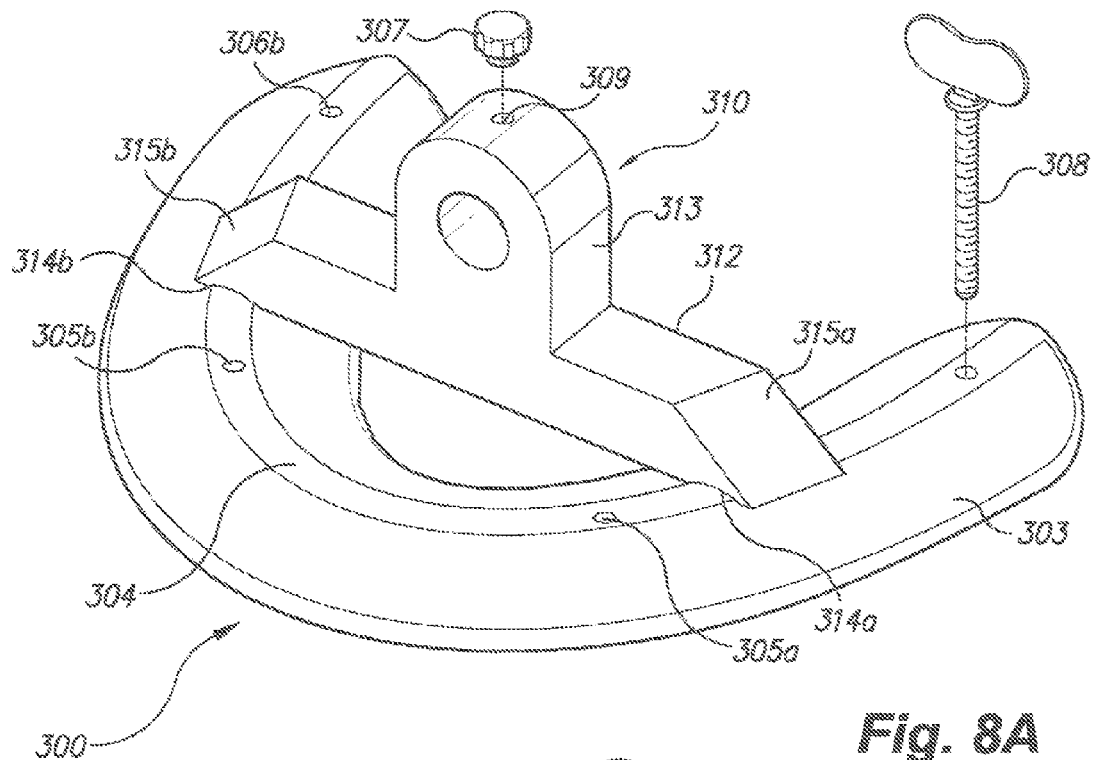
FIG. 8A is a front environmental perspective view of the arched bridge attachment of the dental prosthetic and restoration removal system according to the present invention.
Figure 8B:
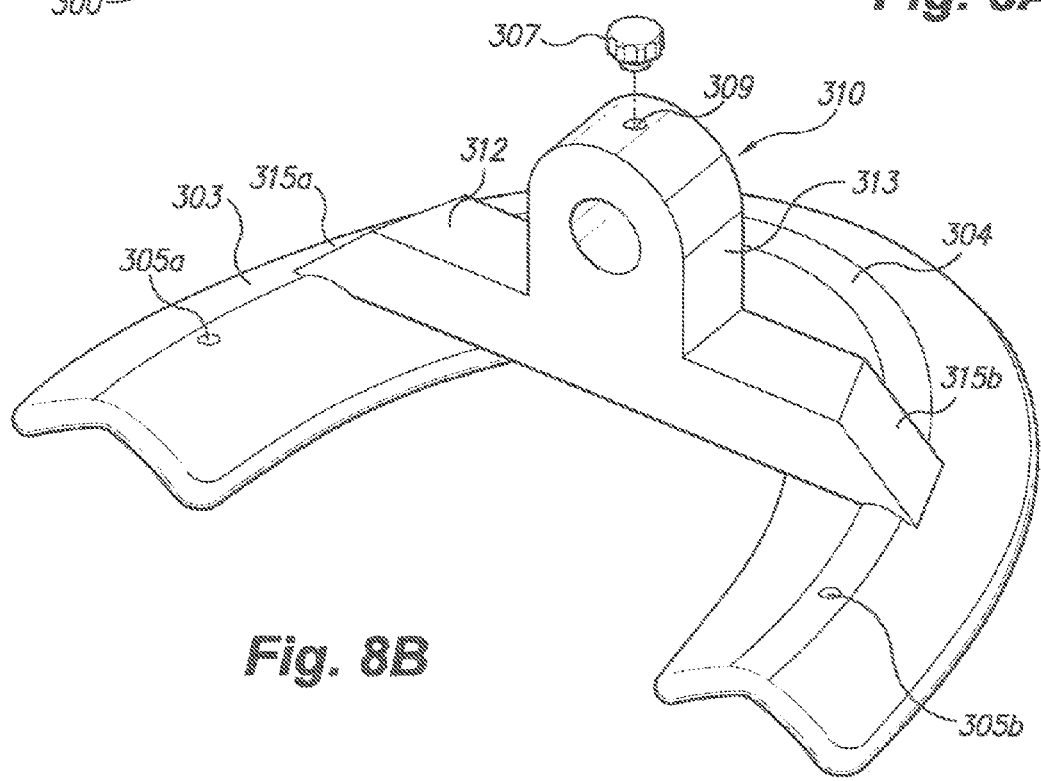
FIG. 8B is a rear environmental perspective view of the arched bridge attachment of the dental prosthetic and restoration removal system according to the present invention.

Referring to FIGS. 8A-8B, an alternative means for removing a total arch bridge is taught. The total arch bridge attachment 300 includes an arcuate member 303 having an integral crown member 310 disposed thereon. Arcuate member 303 has a general horseshoe configuration where a planar surface 304 defines the top of the upper surface created by the arcuate channel design of the underside of arcuate member 303. The arcuate channel design of underside of arcuate member 303 is contoured to receive a total arch bridge. The crown member 310 has a central body 313 having a barrel sleeve housing supported atop a base 312 that spans across arcuate member 303 with notched ends 314a,314b to support crown member 310 atop planar surface 304. The barrel sleeve 313 has an opening for receiving the distal end of a cylindrical support arm (not shown here). Once the support arm is inserted through the opening of the barrel sleeve 313, a threaded fastener 307 is received in a threaded aperture 309 disposed through the midpoint of top wall of barrel sleeve 313 until threaded fastener 307 securely engages the support arm to secure placement of total arch bridge attachment 300 thereto. The proximate end of the support arm (not shown here) can be coupled to a conventional force mechanism and subsequently inserted in the oral cavity of a patient. The opposing ends 315a,315b of base 312 are downwardly angled to provide less obstructions as total arch bridge attachment 300 is inserted in the oral cavity of a patient.

In the event the proprietary adhesive (not shown here) placed on the underside of total arch bridge attachment 300 has bonded total arch bridge attachment 300 to the engaged bridge or applicable dental prosthetic or restoration, the dental practitioner may not be able to remove total arch bridge attachment 300 with the preferred method, but still must take proper care not to disturb the underlying teeth in a manner that will damage or improperly extract the teeth. Emergency removal is appropriate in this instance. The upper surface of arcuate member 300 includes planar surface 304 that has a plurality of threaded apertures 305a,305b,306a,306b disposed through planar surface 304 to underside of arcuate member 300. Threaded apertures 305a,305b are correspondingly disposed on opposite sides of the proximate apex of arcuate member 300. Threaded apertures 306a,306b are correspondingly disposed on the opposing distal ends of arcuate member 300. Tightening screw 57 and the support arm are removed from total arch bridge attachment 300 by the dental practitioner. Emergency removal screws 45 can be introduced through and threadingly mated with one or all threaded apertures 305a,305b,306a,306b in arcuate member 300 as needed. As the inserted emergency removal screw(s) 45 is manually engaged, the distal end of emergency removal screw 45 penetrates the proprietary adhesive substance until the distal end is supported atop the targeted arch bridge. Subsequently, anterior tooth attachment 100 is urged off the targeted arch bridge in a cervico-occlusal direction. Thus allowing the dental practitioner to manually extract total arch bridge attachment 300 from the oral cavity with minimal to no damage to the engaged arch bridge or applicable dental prosthetic or restoration.

Figure 9A:
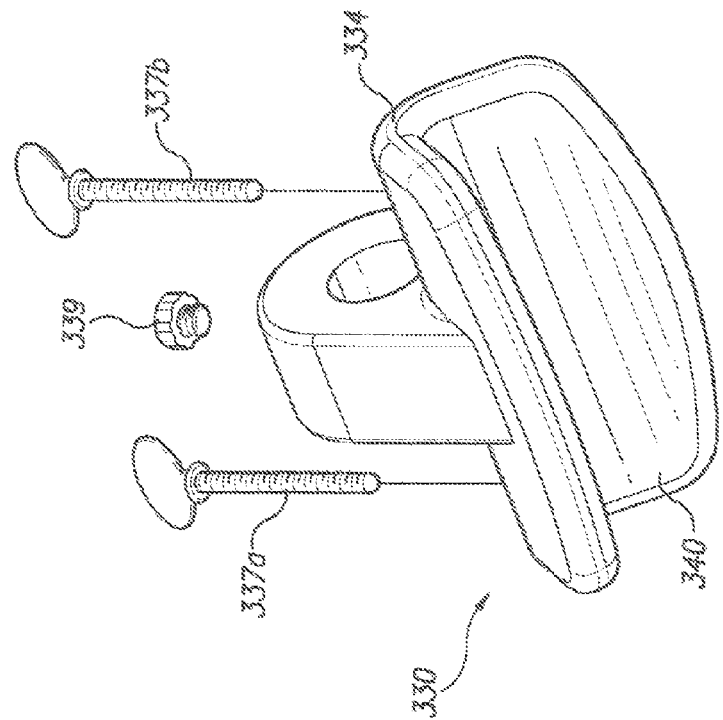
FIG. 9A is a top environmental perspective view of an alternative embodiment of the posterior attachment of the dental prosthetic and restoration removal system according to the present invention.
Figure 9B:
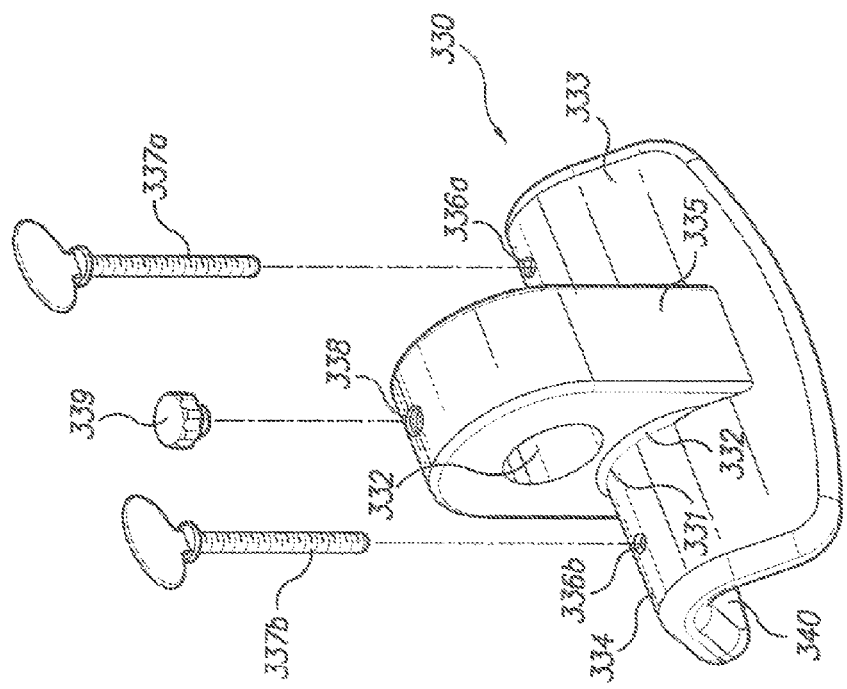
FIG. 9B is a bottom environmental perspective view of an alternative embodiment of the posterior attachment of the dental prosthetic and restoration removal system according to the present invention.

Referring to FIGS. 9A-9B, an alternative posterior tooth attachment 330 for removing a posterior crown or applicable dental prosthetic or restoration is taught. The posterior tooth attachment 330 includes an arched member 333 having an integral crown member 335 centrally disposed on the apex of arched member 333 thereon. Arched member 333 has an arcuate channel configuration contoured to receive a posterior crown or applicable dental prosthetic or restoration. The crown member 335 has a central body having a barrel sleeve housing centrally supported atop the apex of arched member 333 with the base 331 of crown member 335 contoured for snug engagement to apex of arched member 333. The barrel sleeve housing of crown member 335 has an opening 332 for receiving the distal end of a cylindrical support arm (not shown here). Once the support arm is inserted through opening 332 of the barrel sleeve housing, a threaded fastener 339 is received in a threaded aperture 338 disposed through the midpoint of top wall of barrel sleeve housing until threaded fastener 339 securely engages the support arm to secure placement of posterior tooth attachment 330 thereto. The proximate end of the support arm (not shown here) can be coupled to a conventional force mechanism and subsequently inserted in the oral cavity of a patient.

In the event the proprietary adhesive (not shown here) placed on the underside of posterior tooth attachment 330 has bonded posterior tooth attachment 330 to the engaged posterior crown or applicable dental prosthetic or restoration, the dental practitioner may not be able to remove posterior tooth attachment 330 with the preferred method, but still must take proper care not to disturb the underlying teeth in a manner that will damage or improperly extract the teeth. Emergency removal is appropriate in this instance. The upper surface of arched member 333 includes an apex that has a pair of threaded apertures 336a,336b disposed through the apex to underside of arched member 333. Threaded apertures 336a, 336b are correspondingly disposed near the opposing ends of arched member 333. Tightening screw 339 and the support arm are removed from posterior tooth attachment 330 by the dental practitioner. Elongated emergency removal screws 337a,337b can be introduced through and threadingly mated with one or both threaded apertures 336a,336b in arched member 333 as needed. As the inserted emergency removal screw(s) 337a,337b is manually engaged, the distal end of emergency removal screw(s) 337a,337b penetrates the proprietary adhesive substance until the distal end is supported atop the targeted posterior crown or applicable dental prosthetic or restoration. Subsequently, posterior tooth attachment 330 is urged off the targeted posterior crown or applicable dental prosthetic or restoration in a cervico-occlusal direction. Thus allowing the dental practitioner to manually extract posterior tooth attachment 330 from the oral cavity with minimal to no damage to the engaged posterior crown or applicable dental prosthetic or restoration.

Figure 11:
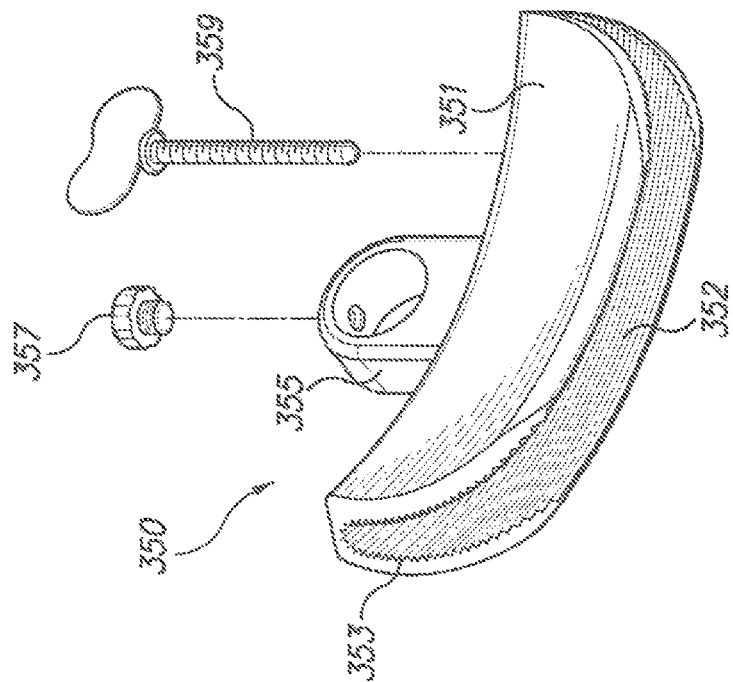
FIG. 11 is a bottom environmental perspective view of an alternative embodiment of the anterior arch attachment of the dental prosthetic and restoration removal system according to the present invention.
Figure 10:
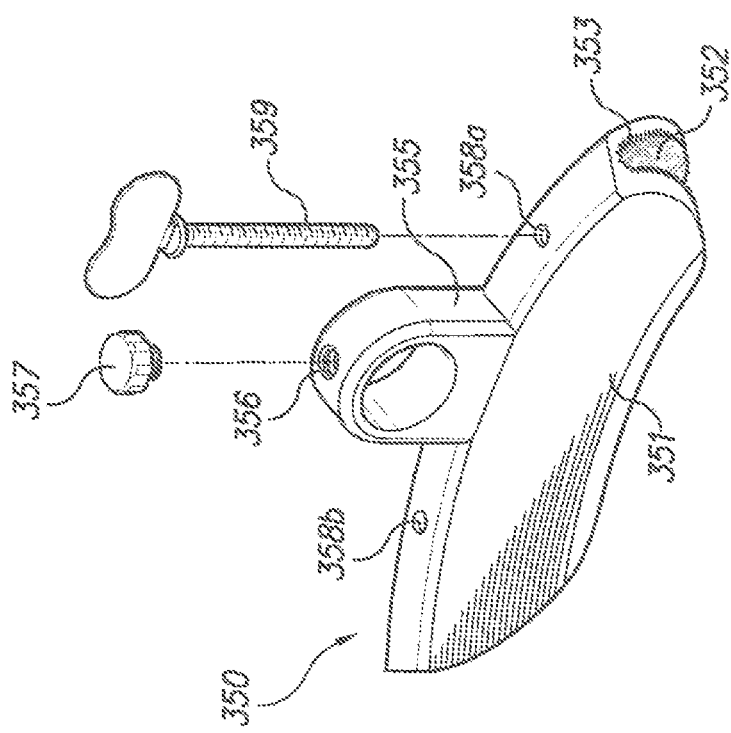
FIG. 10 is a top environmental perspective view of an alternative embodiment of the anterior arch attachment of the dental prosthetic and restoration removal system according to the present invention.

Referring to FIGS. 10-11, an alternative anterior teeth attachment 350 for removing an anterior crown or applicable dental prosthetic or restoration is taught. The anterior teeth attachment 350 includes an arcuate member 351 having a generally U-shaped channel configuration that supports an integral crown member 355 centrally disposed on the top wall of arcuate member 351. The underside of arcuate member 351 is defined by a plurality of recessed grooves 353 that span the length of the underside and facilitate holding a proprietary adhesive substance (not shown here) applied thereto. Arcuate member 351 has a U-shaped channel configuration contoured to receive an anterior crown or applicable dental prosthetic or restoration. The crown member 355 has a central body having a barrel sleeve housing centrally integrally supported atop the top wall of arcuate member 351. The barrel sleeve housing of crown member 355 has an opening for receiving the distal end of a cylindrical support arm (not shown here). Once the support arm is inserted through opening of the barrel sleeve housing 355, a threaded fastener 357 is received in a threaded aperture 356 disposed through the midpoint of top wall of barrel sleeve housing until threaded fastener 357 securely engages the support arm to secure placement of anterior teeth attachment 350 thereto. The proximate end of the support arm (not shown here) can be coupled to a conventional force mechanism and subsequently inserted in the oral cavity of a patient.

In the event the proprietary adhesive (not shown here) placed on the underside of anterior teeth attachment 350 has bonded anterior teeth attachment 350 to the engaged anterior crown or applicable dental prosthetic or restoration, the dental practitioner may not be able to remove anterior teeth attachment 350 with the preferred method, but still must take proper care not to disturb the underlying teeth in a manner that will damage or improperly extract the teeth. Emergency removal is appropriate in this instance. The upper surface of arched member 351 includes a pair of threaded apertures 358a,358b disposed through the top wall of arcuate member 351. Threaded apertures 336a,336b are correspondingly disposed between barrel housing 355 and the respective opposing ends of arched member 351. Tightening screw 357 and the support arm are removed from anterior teeth attachment 350 by the dental practitioner. Elongated emergency removal screws 359 can be introduced through and threadingly mated with one or both threaded apertures 358a,358b in arched member 351 as needed. As the inserted emergency removal screw(s) 359 is manually engaged, the distal end of emergency removal screw(s) 359 penetrates the proprietary adhesive substance until the distal end is supported atop the targeted anterior crown or applicable dental prosthetic or restoration. Subsequently, anterior teeth attachment 350 is urged off the targeted anterior crown or applicable dental prosthetic or restoration in a cervico-occlusal direction. Thus allowing the dental practitioner to manually extract anterior teeth attachment 350 from the oral cavity with minimal to no damage to the engaged anterior crown or applicable dental prosthetic or restoration.

Figure 12:
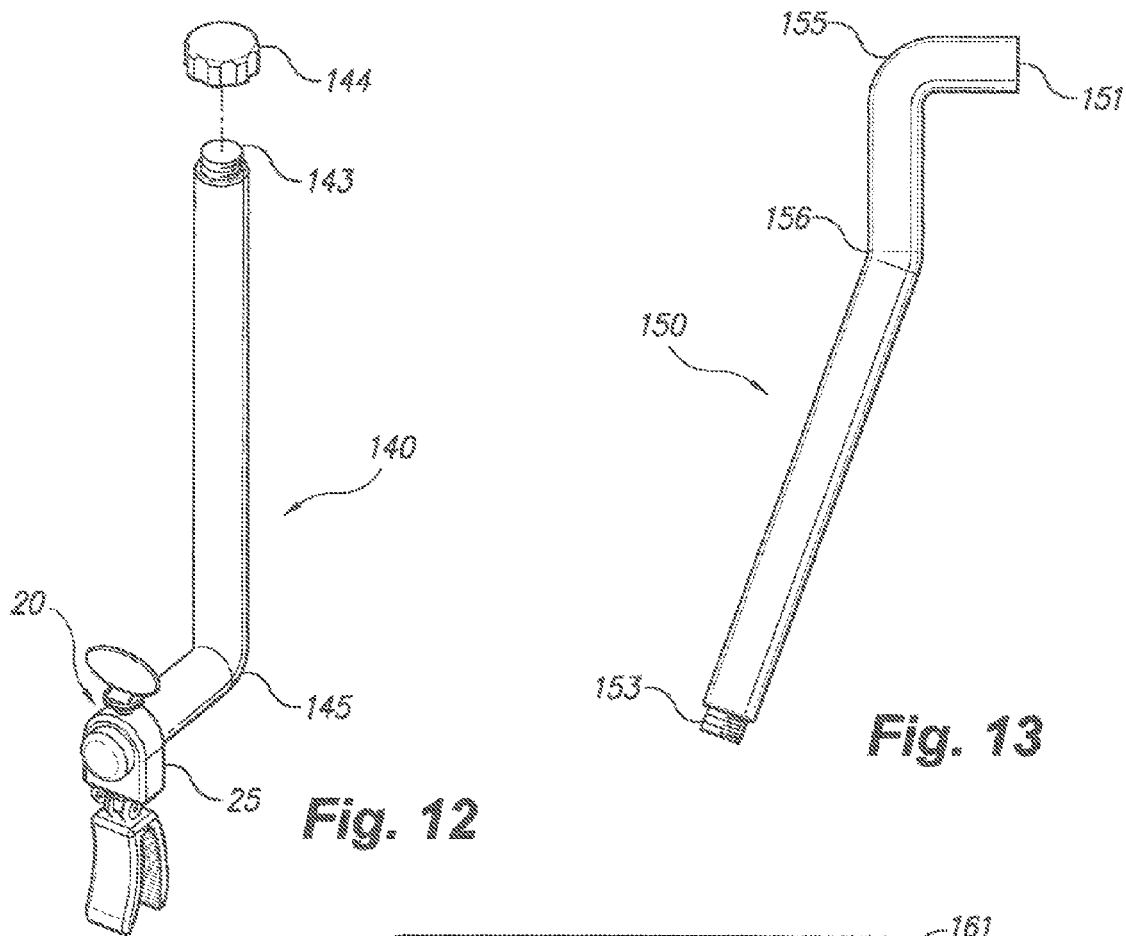
FIG. 12 is an environmental perspective view of an anterior mandibular force bar of the dental prosthetic and restoration removal system according to the present invention.

Referring to FIG. 12, an anterior mandibular force bar 140 is releasably coupled to anterior tooth attachment 20. Anterior mandibular force bar 140 is a generally elongated L-shaped cylindrical construction having a distal end that is received in the crown member 25 of anterior tooth attachment 20 and a threaded proximate end 143 for coupling a force mechanism thereto. Anterior mandibular force bar 140 is designed to allow cervico-occlusal force to be applied to a crown while the anterior tooth attachment 20 distributes the tooth-engaging member 21 to almost the entire buccal, incisal and lingual aspects of an anterior mandibular crown via a proprietary adhesive substance (not shown here) that is thermally treated and placed on the underside 22 of tooth-engaging member 21.

Figure 13:
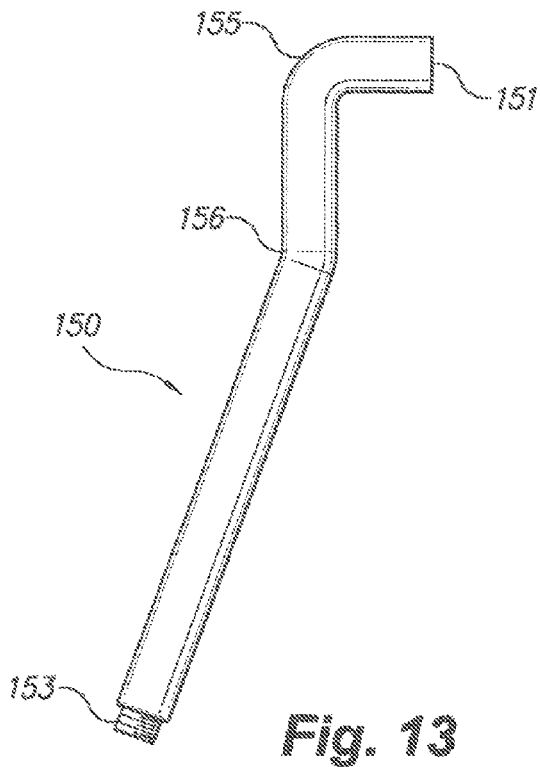
FIG. 13 is an environmental perspective view of an anterior maxillary force bar of the dental prosthetic and restoration removal system according to the present invention.

Referring to FIG. 13, an anterior maxillary force bar 150 is shown that can be attached to an anterior tooth attachment 20. Anterior maxillary force bar 150 is a generally elongated L-shaped cylindrical construction. The distal end of anterior maxillary force bar 150 is designed to be received through opening in crown member 25 of anterior tooth attachment 20 and the proximate end angularly depends from the longitudinal axis of a segment of the distal end. The proximate end 153 is threaded for coupling a force mechanism thereto. Anterior maxillary force bar 150 is designed to allow cervico-occlusal force to be applied to a crown while the anterior tooth attachment 20 distributes the tooth-engaging portion to almost the entire buccal, incisal and lingual aspects of an anterior mandibular crown via a proprietary adhesive substance (not shown here) that is treated and placed on the underside of said portion.

The anterior mandibular force bar and the anterior maxillary force bar can be interchangeably coupled to the anterior teeth attachment 90 as seen in FIGS. 2A-2B.

Figure 14:
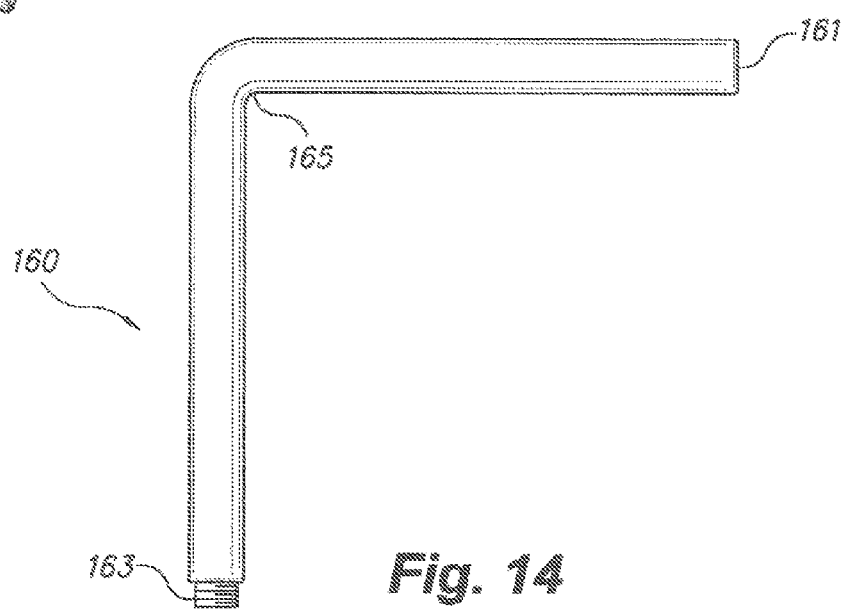
FIG. 14 is an environmental perspective view of a posterior force bar of the dental prosthetic and restoration removal system according to the present invention.

As seen in FIG. 14, a posterior maxillary/mandibular force bar 160 used to attach a posterior tooth attachment 50,70. Posterior anterior maxillary/mandibular force bar is a generally elongated L-shaped cylindrical construction. The distal end of posterior maxillary/mandibular force bar 160 is designed to be received through opening in upper portion 54,74 of posterior tooth attachment 50,70, respectively. The proximate end perpendicularly extends from distal end. The proximate end 163 is threaded for coupling a force mechanism thereto. Posterior maxillary/mandibular force bar 160 is designed to allow cervico-occlusal force to be applied to a crown while the posterior tooth attachment 50,70 distributes the engaging underside area 53,73 to almost the entire buccal, occlusal and lingual aspects of a posterior mandibular or maxillary crown via a proprietary adhesive substance (not shown here) that is treated and placed on the underside 53,73 of posterior tooth attachment 50,70.

Figure 15:
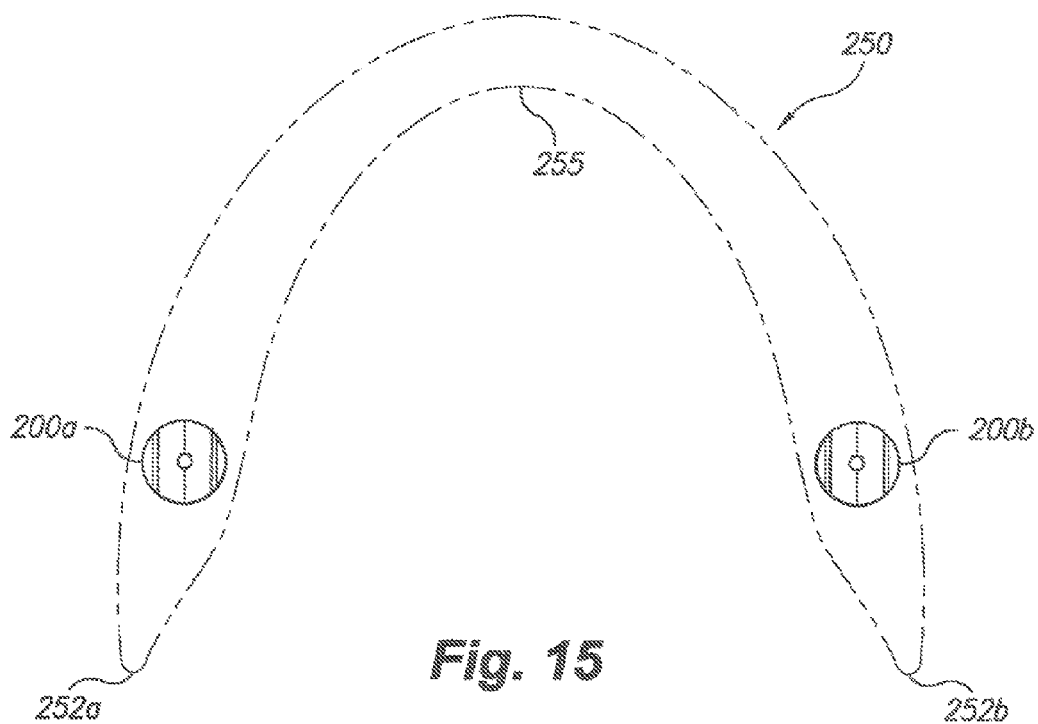
FIG. 15 is a bottom plan view of an alternative embodiment of the arched bridge attachment of the dental prosthetic and restoration removal system according to the present invention.

As seen in FIG. 15, a top view, an arcuate maxillary/mandibular teeth attachment 250 comprises a generally U-shaped construction 255 that is designed to attach to an entire arch maxillary or mandibular crown (or applicable dental prosthetic or restoration) via a proprietary adhesive substance (not shown here) that is treated and placed on the underside of arcuate maxillary/mandibular teeth attachment 250. With no buccal and lingual sides, maxillary/mandibular teeth attachment 250 is designed to distribute cervico-occlusal force to an entire arch equally and attaches to the occlusal region (posterior teeth) and incisal region (anterior teeth—which will involve slight inciso-buccal and inciso-lingual surfaces of the entire arch respectively) via a uniquely shaped proprietary adhesive substance (not shown here) that is thermally treated and placed on the underside of the arched maxillary/mandibular teeth attachment. The proprietary adhesive substance can be placed directly on the tooth or forcibly applied to the underside of maxillary/mandibular teeth attachment 250 in order to temporarily couple the maxillary/mandibular teeth attachment 250 to the occlusal and incisal regions or to couple the respective portions before cervico-occlusal force is used. The respective distal ends 252a,252b of the maxillary/mandibular teeth attachment 250 integrally include an alternative posterior tooth attachment 200, as best seen in FIGS. 16 and 18A-18C. Maxillary/mandibular teeth attachment 250 is ideally used in conjunction with central holder 12 and the depending plurality of elongated support arms 59,79 without anterior tooth attachment 20 and posterior tooth attachments 50,70. This top view of maxillary/mandibular teeth attachment 250 also shows the threaded apertures 200a,200b designed to receive a tightening screw (not shown here) or an emergency removal screw (not shown here) when the applicable support arm is inserted or removed, respectively, from the barrel sleeves of the crowns in quadrant tooth attachments 200a,200b as used in maxillary/mandibular teeth attachment 250.

Figure 16:
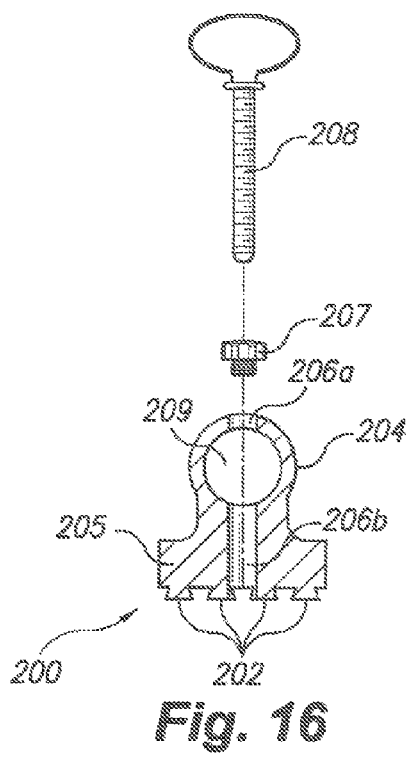
FIG. 16 is a cross-sectional view of the quadrant tooth attachment of the dental prosthetic and restoration removal system according to the present invention.

As seen FIG. 16, a quadrant tooth attachment 200 is shown. Quadrant tooth attachment 200 includes a cylindrical base 205 which supports an integral barrel sleeve housing 204 on the upper surface and includes an underside defined by no buccal or lingual sidewalls and by a plurality of recessed grooves 202 that extend the length of the underside for greater retention of a proprietary adhesive substance (not shown here) applied to the underside. A threaded aperture 206a,206b extends vertically throughout the midpoint of quadrant tooth attachment 200. Quadrant tooth attachment 200 is ideally used for posterior bridge removal and attaches preferably to the occlusal aspect of the bridge. When a support arm or force bar is introduced through the opening 209 of the integral barrel sleeve 204 of the upper surface, a tightening screw 207 is introduced through threaded aperture 206a disposed in the top of the integral barrel sleeve 204 until tightening screw 207 engages the support arm or force bar to releasably secure the position of the quadrant tooth attachment 200 on support arm or force bar.

In the event the proprietary adhesive substance placed on the underside of the quadrant tooth attachment 200 has bonded quadrant tooth attachment 200 to the engaged dental prosthetic or restoration—the dental practitioner may not be able to quadrant tooth attachment 200 with the preferred method, but still must take proper care not to torque or luxate the underlying tooth or teeth in a manner that will damage or improperly extract said tooth or teeth. Hence, tightening screw 207 and support arm/force bar must be removed and an elongated emergency removal screw 208 can be introduced through the threaded aperture 206*a* in the top wall of integral barrel sleeve 204 and mated with the corresponding threaded aperture 206*b* disposed through base 205. This allows the dental practitioner to manually extract the quadrant tooth attachment 200 from the oral cavity with minimal to no damage to the engaged dental prosthetic or restoration or teeth. This embodiment of the quadrant tooth attachment 200 and the accompanying uniquely shaped proprietary adhesive substance 203 are further discussed below.

Figure 17:
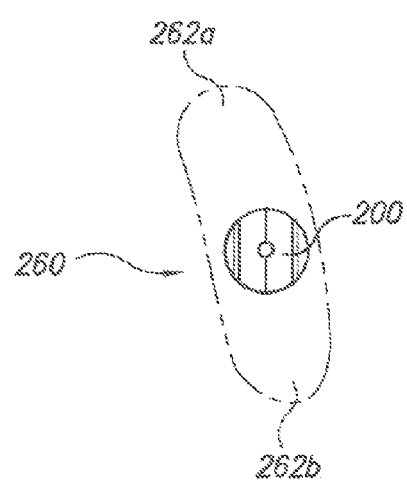
FIG. 17 is a top plan view of the quadrant tooth attachment of the dental prosthetic and restoration removal system according to the present invention.

Referring to FIG. 17, another application 260 of the quadrant tooth attachment 200 is used for posterior bridge removal and attaches to the occlusal aspect of the bridge only with no buccal or lingual attachment sides. Posterior bridge removal device 260 includes a contoured oblong base which supports a quadrant tooth attachment 200 having an integral barrel sleeve on the upper surface and includes an underside that may be defined by a plurality of recessed grooves that extend longitudinally for greater retention of a proprietary adhesive substance applied to the underside. As seen in this top view, a threaded aperture extends vertically throughout the midpoint of the quadrant tooth attachment 200. Posterior bridge removal device 260 is ideally used for posterior bridge removal and attaches preferably to the occlusal aspect of the bridge. When a force bar is introduced through the proximate end of the integral barrel sleeve of the upper surface of quadrant tooth attachment 200, a tightening screw (not shown here) is introduced through the threaded aperture disposed in the top of the integral barrel sleeve until the tightening screw engages the force bar to releasably secure the position of the posterior tooth attachment on said force bar.

In the event the proprietary adhesive substance placed on the underside of the posterior bridge removal device 260 has bonded the posterior bridge removal device 260 to the engaged posterior bridge—the dental practitioner may not be able to remove posterior bridge removal device 260 with the preferred method, but still must take proper care not to torque or luxate the underlying tooth or teeth in a manner that will damage or improperly extract said tooth or teeth. Hence, the tightening screw and force bar must be removed and an emergency removal screw can be introduced through the threaded aperture in the upper portion and mated with the corresponding threaded aperture in the lower portion of quadrant tooth attachment 200. This allows the dental practitioner to manually extract the posterior bridge removal device 260 from the oral cavity with minimal to no damage to the engaged bridge or teeth.

It is important to note that the system for removal of dental prosthetics and restorations of the present invention can be made entirely from disposable materials or particular components can be made disposable to reduce costs.

An alternative application of the proprietary adhesive substance features a safety tab made of a biodegradable cloth inserted in the proprietary adhesive substance and used as a means to exert more control over the digital manipulation of the proprietary adhesive substance. A flexible elongate can be tethered to the safety tab at one end and to a safety ring at the opposing end. The safety ring may be engaged with a finger to prevent a removed crown from inadvertently slipping into the oral cavity of the patient and possibly being ingested—perhaps even resulting in the constriction of an airway. This configuration allows the dental practitioner to remove the safety tab and proprietary adhesive substance from the oral cavity of a patient. Moreover, a separation matrix can be used in concert with the proprietary adhesive substance to prevent the proprietary adhesive substance from contacting adjacent teeth. The separation matrix is a single foldable assembly of flaccid or semi-rigid material folded along the midpoint of the assembly such that the two halves, where a first half is contoured, can be perpendicularly oriented with respect to one another. The second half of the separation matrix is inserted in an occluso-cervical direction to cover the occlusal or incisal surfaces of the teeth adjacent to dental structure targeted for removal, such that the proprietary adhesive substance will not attach to any aspects of the adjacent teeth.

Another practical use for the present invention is to extract primary teeth and permanent teeth with periodontal involvement. A fine cloth material is placed on the plastic components with a polymer cement such that the cloth may can treated with a chemical agent to improve the adhesive attachment to the plastic or polymer components.

An alternative embodiment of the proprietary adhesive substance is a sugar-based composition, similar to conventional sticky candies, that it will biodegradable. This embodiment of the proprietary adhesive substance is ideal in the case of an emergency (e.g., diabetic seizure). The proprietary adhesive substance can be administered under the tongue and dissolved with a steady stream of water, thus preventing the dental practitioner from having to use a rotary instrument to remove the device.

The foregoing description has been limited to specific embodiments of this invention. It will be apparent; however, that variations and modifications may be made by those skilled in the art to the disclosed embodiments of the invention, with the attainment of some or all of its advantages and without departing from the spirit and scope of the present invention. For example, multiple components of the present invention can be uniquely arranged in a compartmentalized storage case for transport. Moreover, the present invention could possibly be releasably attached to a dent in an automobile and used to pull a dent out of an automobile with the exertion of the proper force. Additional embodiments of the present invention may teach other tooth/teeth attachments of varying dimensions that can be used in conjunction with the central holder for patients having small to large oral cavities/teeth or for canine and/or pre-molar teeth.

These and other features of the present invention will become readily apparent upon further review of the attached drawings.

It will be understood that various changes in the details, materials, methods, and arrangements of the dental prosthetic or restoration removal system 10 which have been generally described above and detailed in the attached drawings in order to explain the nature of this invention may be made by those skilled in the art without departing from the principle and scope of the invention.

I claim:

1. A system for removing dental prosthetics and restorations, said system comprising:
    a) a central holder comprising a generally triangular housing for receiving and securely supporting a single or plurality of L-shaped support arms in a spaced apart arrangement, each L-shaped support arm is capable of supporting an attachment designed to adhesively engage and remove a dental prosthetic and restoration with the application of force;

b) a first L-shaped support arm releasably and adjustably attached to said central holder at one end and designed to support a posterior tooth attachment on the opposing end;

c) a second L-shaped support arm releasably and adjustably attached to said central holder at one end and designed to support a posterior tooth attachment on the opposing end;

d) a third L-shaped support arm releasably and adjustably attached to said central holder at one end and designed to support an anterior tooth attachment on the opposing end; and e) a force arm releasably and adjustably attached to said central holder at one end and on an opposite side from at least one of said first support arm, said second support arm, and said third support arm.

2. The system for removing dental prosthetics and restorations, as set forth in claim 1 the posterior tooth attachment further comprising an adjustable body for accommodating dental prosthetics and restorations of varying sizes and spatial orientations and means for emergency removal.

3. The system for removing dental prosthetics and restorations, as set forth in claim 1 the anterior tooth attachment further comprising a pivoting body designed to accommodate a dental prosthetic and restoration of varying size and spatial orientation on a single anterior tooth and means for emergency removal.

4. The system for removing dental prosthetics and restorations as set forth in claim 1, wherein said central holder is formed of disposable material; said first L-shaped support arm is formed of disposable material; said second L-shaped support arm is formed of disposable material; said third L-shaped support arm is formed of disposable material; and said force arm is formed of disposable material.

5. A dental prosthetics and restorations removal system to effectively and efficiently remove a plurality of dental prosthetics and restorations without damaging the dental prosthetics and restorations, and with minimal discomfort to a dental patient, said system comprising:

a) a holder having a generally triangular housing for supporting a plurality of L-shaped support arms in a regularly spaced arrangement, each of said L-shaped support arms capable of supporting an attachment for engaging a dental prosthetic and restoration;

b) a first arm of said plurality of L-shaped support arms releasably and adjustably attached to said central holder at one end;

c) a first posterior tooth attachment supported on the opposing end of said first arm;

d) a second arm of said plurality of L-shaped support arms releasably and adjustably attached to said central holder at one end;

e) a second posterior tooth attachment supported on the opposing end of said second arm;

f) a third arm of said plurality of L-shaped support arms releasably and adjustably attached to said central holder at one end;

g) a force application arm releasably and adjustably attached to said central holder in opposition to at least said third arm; and h) an anterior tooth attachment supported on the opposing end of said third arm;

i) each of said first and second posterior tooth attachment, and said anterior tooth attachment designed and configured to adhesively engage a dental prosthetic and restoration.

6. The dental prosthetics and restorations removal system as set forth in claim 5, each said first and second posterior tooth attachment further comprising an adjustable body for accommodating dental prosthetics and restorations of varying sizes and spatial orientations.

7. The dental prosthetics and restorations removal system as set forth in claim 5 said anterior tooth attachment further comprising a pivoting body designed to accommodate a dental prosthetic and restoration of varying size and spatial orientation on a single anterior tooth.

8. The system as set forth in claim 6 wherein said second posterior tooth attachment further comprising means for emergency removal; whereby minimizing the discomfort of a dental patient.

9. The system as set forth in claim 7 wherein said first posterior tooth attachment further comprising means for emergency removal; whereby minimizing the discomfort of a dental patient.

10. The system as set forth in claim 7 wherein said anterior tooth attachment further comprising means for emergency removal; whereby minimizing the discomfort of a dental patient.

11. The system as set forth in claim 5, further comprising a force application arm for imparting manual application of force from one side of said central holder to said anterior tooth attachment on an opposite side of said central holder.

12. The system as set forth in claim 5, further comprising an arcuate teeth attachment, for coupling the maxillary and mandibular teeth, having a generally U-shaped construction and designed and configured for attachment to the entire arch maxillary and mandibular dental prosthetic or restoration, wherein said arcuate teeth attachment distributes cervico-occlusal force over the entire arch equally.

13. The system as set forth in claim 12, including a quadrant tooth attachment for adhesively attaching to a dental prosthetic or restoration to remove the dental prosthetic and restoration with application of said force application arm.

14. A system for removing dental prosthetics and restorations, said system comprising:

a) a central holder comprising a generally triangular shaped housing for receiving and securely supporting a at least a first, a second, and a third L-shaped support arms in a spaced apart arrangement, each said first, said second, and said third L-shaped support arm is capable of supporting an attachment;

b) said first L-shaped support arm releasably and adjustably attached to said central holder at one end and designed to support a first posterior tooth attachment on the opposing end;

c) said second L-shaped support arm releasably and adjustably attached to said central holder at one end and designed to support a second posterior tooth attachment on the opposing end; and d) said third L-shaped support arm releasably and adjustably attached to said central holder at one end and having an anterior tooth attachment supported on the opposing end thereof;

e) wherein said anterior tooth attachment adhesively engages and removes a dental prosthetic and restoration with the application of force;

f) where said system may be disposable.

15. The system as set forth in claim 14, further comprising an arm for releasably and adjustably attaching to said central holder on an opposite side of said central holder from at least said anterior tooth attachment for applying force across said central holder and to said anterior tooth attachment, whereby said anterior tooth attachment inserts or removes dental prosthetics and restorations.

16. The system as set forth in claim 14, wherein said first posterior tooth attachment further comprising an adjustable body for accommodating dental prosthetics and restorations of varying sizes and spatial orientations and means for emergency removal.

17. The system as set forth in claim 14, wherein said anterior tooth attachment further comprising a pivoting body designed to accommodate a dental prosthetic and restoration of varying size and spatial orientation on a single anterior tooth and means for emergency removal.

18. The system as set forth in claim 16 wherein said second posterior tooth attachment further comprising an adjustable body for accommodating dental prosthetics and restorations of varying sizes and spatial orientations and means for emergency removal.

19. The system as set forth in claim 17 wherein said first posterior tooth attachment further comprising an adjustable body for accommodating dental prosthetics and restorations of varying sizes and spatial orientations and means for emergency removal.

20. The system as set forth in claim 17 wherein said second posterior tooth attachment further comprising an adjustable body for accommodating dental prosthetics and restorations of varying sizes and spatial orientations and means for emergency removal.

* * * * *